United States Patent [19]

Klepak et al.

[11] 4,033,365

[45] July 5, 1977

[54] FLAVORED DENTAL ARTICLES

[75] Inventors: Philip B. Klepak, Bloomsbury; David I. Richardson, Somerset; Robert G. Fourman, East Brunswick, all of N.J.

[73] Assignee: Johnson & Johnson, New Brunswick, N.J.

[22] Filed: Jan. 23, 1976

[21] Appl. No.: 651,766

[52] U.S. Cl. .................................................. 132/89
[51] Int. Cl.² ........................................ A61C 15/00
[58] Field of Search ........................... 132/89, 90

[56] References Cited

UNITED STATES PATENTS

| | | | |
|---|---|---|---|
| 174,619 | 3/1876 | Clark, Jr. | 132/89 |
| 410,794 | 9/1889 | Hellwig | 132/89 |
| 3,800,812 | 4/1974 | Jaffe | 132/89 |
| 3,830,246 | 8/1974 | Gillings | 132/89 |
| 3,838,702 | 10/1974 | Standish | 132/89 |
| 3,913,596 | 10/1975 | Stuart | 132/89 |
| 3,943,949 | 3/1976 | Ashton | 132/89 |

*Primary Examiner*—G.E. McNeill
*Attorney, Agent, or Firm*—Steven P. Berman

[57] ABSTRACT

A stabilized, flavored dental article for cleaning the interproximal surfaces of the teeth such as dental floss or dental tape comprising filaments with a non-wax polymeric coating containing spray-dried flavor particles.

12 Claims, No Drawings

FLAVORED DENTAL ARTICLES

BACKGROUND OF THE INVENTION

This invention relates to articles for cleaning the interproximal surfaces of the teeth and more particularly to flavored dental floss and dental tape.

It has been shown that tooth decay and dental disease can be attributed to bacterial action resulting from the formation of plaque about the teeth and/or the entrapment of food particles between the teeth and interstices therebetween. The removal of plaque and entrapped food particles reduces caries, reduces the tendency towards gingivitis, and reduces mouth odor as well as generally improving oral hygiene. Conventional brushing of the teeth has been found to be unsatisfactory to effect the removal of entrapped food particles from some crevices between the teeth and/or to effectively remove the plaque by which the bacteria adheres to the teeth. To supplement brushing, various materials have been used to clean the interproximal spaces and surfaces of the teeth, for example, dental floss and dental tape. It is to be understood that the use of the term "dental floss" hereinafter encompasses dental tape as well as any similar article.

The use of a flavored dental floss as opposed to the more common unflavored variety provides aesthetic advantages to the floss making the use of said floss more pleasant thereby encouraging better oral hygiene practices.

Many people also prefer an unwaxed floss to a waxed floss since an unwaxed floss is a thinner product than the same denier waxed counterpart and those with tight interproximal contacts often find it easier to use. Also, some people have the unsubstantiated belief that flossing with a waxed floss may leave residues of wax on the teeth which may be harmful whereas others merely do not like the waxy taste in their mouths.

Prior art dental floss and dental tape products have explored the possibilities of adding various flavors in their production in an attempt to impart a flavor to the finished product. Such products have usually been prepared by the direct addition of flavor oils to the yarn or, in the case of a waxed floss product, the addition of the flavor oils to the wax used to coat the floss. The disadvantage of the direct addition of the flavor oils is that such oils are in most cases volatile and very reactive. As a result of the volatility and reactiveness of these flavor oils, the flavor impression is rapidly lost from the product in a relatively short period of time. Thus, in view of the manufacturing, storage and shelf life times of these products, the consumer will not get the benefits of the addition of the flavors to the product. It has also been suggested to incorporate the flavor oils into a non-wax binder material which is then applied to the floss. It has been found, however, that although this process may yield a flavored product, the flavor is rapidly lost and exhibits no stability.

U.S. Pat. No. 3,943,949 issued Mar. 16, 1976, relates to flavored dental articles containing a wax coating on said articles.

Prior to this invention, it does not appear that any non-wax dental floss product was known or available wherein the flavor was stabilized and long-lasting and would not significantly diminish with reasonable shelf-life time and thereby be available when the product was utilized.

SUMMARY OF THE INVENTION

It is an object of this invention to provide improved dental floss and dental tape.

It is another object of this invention to provide flavored dental floss and dental tape wherein said flavors are stabilized and long-lasting.

It is a further object of this invention to provide non-waxed flavored dental floss and dental tape wherein said flavors are stabilized and long-lasting.

It is a still further object of this invention to provide methods of manufacture of non-waxed dental floss and dental tape with long-lasting, stabilized flavors.

Other objects of this invention will be set forth in, or be apparent from, the following detailed description of the invention.

The foregoing objects and other features and advantages of the present invention are achieved by the use of spray-dried flavor particles in conjunction with a specific non-wax polymeric coating to provide a long-lasting, stabilized flavored dental floss. More specifically, the present invention relates to the use of spray-dried flavor particles wherein flavor oils are dispersed in a matrix of a water-soluble medium to protect the flavor oil from volatilization and oxidation thereby forming a spray-dried flavor particle which is capable of providing a long-lasting, stabilized flavor to dental floss. When an individual utilizes the dental floss and the spray-dried flavor particle contacts an aqueous medium, such as saliva, the water-soluble matrix dissolves thereby releasing the desired flavor.

DESCRIPTION OF PREFERRED EMBODIMENTS

A preferred embodiment of the present invention comprises a flavored dental floss formed of a plurality of individual filaments of a substrate material suitable for use as a dental floss. Such substrate materials include high and normal tenacity nylon such as nylon 6 and 66, rayon, Dacron, acetate polymers, polypropylene and the like as well as cotton, wool and other staple fibers. The plurality of individual filaments are formed together to give a larger thread of a sufficiently small diameter to permit insertion in the interproximal areas between the teeth. If desired, the filaments of yarn can be colored utilizing any compatible and accepted color dye such as FD&C Blue No. 1, FD&C Yellow No. 5, FD&C Red No. 40, mixtures thereof and the like.

It is preferred to twist the individual filaments to form the floss in order to give the product additional integrity, that is, additional strength to prevent shredding and filament separation. Dental floss can be made without twisting the individual filaments and dental tape is usually made with little or no filament twist. The twist of the filaments can be from about 0.5 to 3.0 turns per inch, with a preferred twist of about 1.5 to 2.0 turns per inch.

The tensile strength of the finished flavored dental floss should be from about 5 to 25 lbs., although higher tensile strengths are acceptable. The tensile strength of the floss is preferably from about 7 to 15 lbs. If a dental floss with a tensile strength of less than about 5 lbs. is prepared, it will break easily and not be satisfactory for use as a floss. Dental floss with tensile strengths greater than 25 lbs. are satisfactory but offer few additional advantages and are less economical to produce. The thickness of the dental floss should be from about 300 to 2,000 denier, preferably from about 500 to 1,500 denier in order to achieve a satisfactory product.

The spray-dried flavor particles are adhered to the surface of or partially or fully embedded in specific non-wax polymeric coatings. The specific non-wax polymeric coatings useful in the present invention must have good adhesion, clarity and toughness as well as being quick-drying, non-tacky and non-toxic. Good adhesion is required to adequately hold the spray-dried flavor particles as well as to bind the individual filaments of the fibers together. The non-wax polymeric coating should have clarity or transparency in order to provide an aesthetic product and prevent interference with the addition of any color to the floss, if such is desired. The coatings should also have a toughness such that upon drying they do not become brittle and crack and flake off when one uses the floss. The non-wax polymeric coatings should also be quick-drying to aid in processing, non-tacky to prevent sticking to one's fingers upon use of the floss and non-toxic.

Specific non-wax polymeric coatings which are useful in the present invention include:

a. alkyl monoesters of poly(methyl vinyl ether/maleic acid) of the formula:

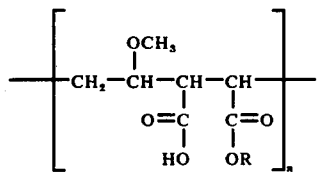

wherein R is an alkyl group containing from 1 to 4 carbon atoms or hydrogen and wherein $n$ is from about 3000 to 3400;

b. polyvinyl pyrrolidones of the formula:

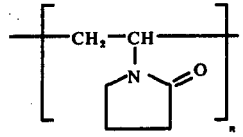

wherein $n$ is from about 100 to 360.

c. acrylamide/acrylate/butylaminoethyl methacrylate polymers. Polymers of this type are sold by National Starch & Chemical Corporation under the trademark "Amphomer;"

d. vinyl acetate/crotonic acid/vinyl neodecanoate terpolymers. Terpolymers of this type are sold by National Starch & Chemical Corporation under the trademark "Resyn 28-2930;"

e. vinyl acetate/crotonic acid copolymers. Copolymers of this type are sold by National Starch & Chemical Corporation under the trademark "Resyn 28-1310;"

f. terpolyamides comprised of the copolymerization products of three polyamide precursers, a dicarboxylic acid-diamine reaction product, a second but dissimilar dicarboxylic acid-diamine reaction product and a lactam wherein said terpolyamides have a molecular weight of from about 12000 to about 24000. Terpolymers of this type are sold by Belding Chemical Industries as BC1-600 series nylon.

The polymeric coating comprises about 1 to 10% by weight of the dental floss, preferably about 2 to 6% by weight. If less than about 1% by weight of the polymeric coating is utilized, there may not be a sufficient amount present to allow the spray-dried flavor particles to sufficiently adhere and if greater than about 10% by weight is present, the resulting floss product may have an undesirable stiff texture flaking of the coating can occur.

The spray-dried flavor particles consist of the flavor oil dispersed in a water-soluble matrix material. Suitable water-soluble materials include gums such as gum acacia, gum arabic, gum tragacanth, and the like; starches such as corn starch; dextrins and the like. Suitable materials for use as flavors are those which allow the user to detect a strong, noticeable flavor while permitting the maintenance of an acceptable product appearance. Such flavors include peppermint, spearmint, wintergreen, cassia, cinnamon, and the like; fruit flavors such as cherry, strawberry, lime; and the like. Preferred flavors for use in dental floss include peppermint and cassia.

The spray-dried flavor particles can be readily prepared by known spray drying procedures. For example, a suitable flavor oil can be mixed with a solution of a water-soluble matrix material and the resulting mixture is then emulsified by mechanical or other means to form an emulsion. The emulsion thus formed is then passed through suitable spray-drying apparatus to flash off the water present in the emulsion resulting in the formation of a spray-dried flavor particle. The spray-dried flavor particles should be of a particle size of from about $44\mu$ to $840\mu$ with particles of $177\mu$ or smaller being preferred. As discussed above, the spray-dried flavor particles consist of a flavor dispersed in the matrix of a water-soluble medium. The flavor comprises from about 10 to 35% by weight of the spray-dried flavor particle and the water-soluble medium comprises from about 90–65% by weight of the spray-dried flavor particle. The spray-dried flavor particle comprises from about 0.5 to 12% by weight of the flavored dental floss product, preferably about 3 to 8% by weight of the floss. If desired, the spray-dried flavor particles can be colored utilizing any compatible and accepted color dye, for example, FD&C Blue No. 1, FD&C Yellow No. 5, FD&C Red No. 40, mixtures thereof and the like.

The stabilized, flavored dental floss of the present invention can be prepared by a number of different methods. One method involves passing the floss through a bath containing the polymeric coating in a suitable solvent, e.g., lower alkanols containing from 1 to 4 carbon atoms. The floss is passed through such a bath, e.g., by means of directed guides, and while the coating is still tacky, the spray-dried flavor particles are sifted or dusted on the coated yarn. The sifting or dusting is controlled to give the desired flavor concentration. The yarn is then passed through an oven or vacuum chamber to dry and flash off the solvent.

Another method of achieving the flavored dental floss of the present invention comprises drawing the coated yarn while it is still tacky through a pile of sifted spray-dried flavor particles permitting the spray-dried flavor particles to adhere to the coating. The yarn is then passed through an oven or vacuum chamber to dry and flash off the solvent.

Still another method of adding the spray-dried flavor particles comprises spraying the flavor particles onto the floss with the polymeric coating as the floss is wound on a rewind supply roll immediately after the coating has occurred. This may also cause some of the spray-dried flavor particles to become partially impregnated in the coating and/or filaments of the floss due to the mechanical compression.

An entirely different method of preparing the flavored dental floss of the present invention involves adding the spray-dried flavor particles directly into the bath containing the polymeric coating in a suitable solvent. The spray-dried flavor particles are mixed with the coating to form a dispersion containing the spray-dried flavor particles dispersed in the coating. The dispersion should be continuously mixed to keep it homogenous. The floss is then passed through the bath, e.g., by means of directed guides, and an excess of polymeric coating containing the spray-dried flavor particles is picked up by the yarn. The solvent is then removed by conventional procedures. The yarn can then pass through various mechanical means to remove any excess coating, resulting in the finished flavored dental floss.

When samples were prepared in accordance with the present invention and aged at temperatures of from 40° F to 140° F for periods of up to 4 months, no significant loss of flavor or other negative features such as unsightly discoloring were observed. Thus, the flavored dental floss products prepared in accordance with the present invention are flavor stabilized. The same test with samples containing non-spray-dried flavors did not result in a flavored dental floss product which was flavor stabilized.

A dental floss or dental tape as described herein exhibits a desirable surface texture and provides excellent cleaning to the interproximal surfaces of the teeth with a desirable flavor being imparted to the teeth and mouth of the user thereof.

In addition to the preferred embodiments described herein, other arrangements and variations within the spirit of the invention and the scope of the appended claims will occur to those skilled in the art.

What is claimed is:

1. A stabilized flavored article for cleaning the teeth comprising a plurality of filaments of a substrate material formed into a larger thread of a sufficiently small diameter to permit insertion between the teeth, said thread impregnated with a polymeric coating containing spray-dried flavor particles, wherein the polymeric coating is selected from the group consisting of
   a. alkyl monoesters of poly(methyl vinyl ether/maleic acid) of the formula:

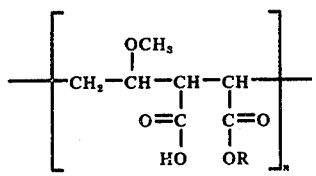

wherein R is an alkyl group containing from 1 to 4 carbon atoms or hydrogen and wherein $n$ is from about 3000 to 3400;
   b. polyvinyl pyrrolidones of the formula:

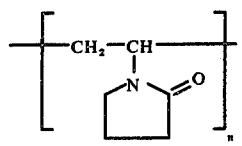

wherein $n$ is from about 100 to 360;
   c. acrylamide/acrylate/butylaminoethyl methacrylate polymers;
   d. vinyl acetate/crotonic acid/vinyl neodecanoate terpolymers;
   e. vinyl acetate/crotonic acid copolymers; and
   f. terpolyamides comprised of the copolymerization products of dicarboxylic acid-diamine reaction product, a second but dissimilar dicarboxylic acid-diamine reaction product and a lactam wherein said terpolyamides have a molecular weight of from about 12000 to about 24000.

2. The stabilized flavored article of claim 1 wherein the spray-dried flavor particles consist essentially of a flavor oil dispersed in a matrix of a water soluble medium.

3. The stabilized flavored article of claim 1 wherein the polymeric coating is an alkyl monoester of poly(methyl vinyl ether/maleic acid) of the formula:

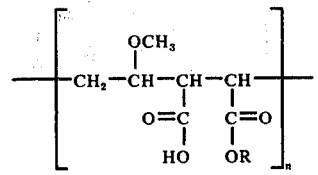

wherein R is selected from alkyl groups containing 1 to 4 carbon atoms and hydrogen and $n$ is from 3000 to 3400.

4. The stabilized flavored article of claim 1 wherein the polymeric coating is a polyvinyl pyrrolidone of the formula:

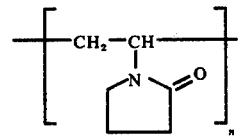

wherein $n$ is from about 100 to 360.

5. The stabilized flavored article of claim 1 wherein the polymeric coating is an acrylamide/acrylate/butylaminoethyl methacrylate polymer.

6. The stabilized flavored article of claim 1 wherein the polymeric coating is a vinyl acetate/crotonic acid/vinyl neodecanoate terpolymer.

7. The stabilized flavored article of claim 1 wherein the polymeric coating is a vinyl acetate/crotonic acid copolymer.

8. The stabilized flavored article of claim 1 wherein the polymeric coating is a terpolyamide comprising the copolymerization product of a dicarboxylic acid-diamine reaction product, a second but dissimilar dicarboxylic acid-diamine reaction product and a lactam wherein said terpolyamides have a molecular weight of from about 12000 to about 24000.

9. The stabilized flavored article of claim 2 wherein the spray-dried flavor particles comprise about 0.5 to 12% by weight of the stabilized flavored article.

10. The stabilized flavored article of claim 1 wherein the polymeric coating comprises about 1 to 10% by weight of the stabilized flavored article.

11. The stabilized flavored article of claim 1 wherein the plurality of filaments are colored with a suitable color dye.

12. A stabilized flavored article for cleaning the teeth comprising a plurality of filaments of a substrate material formed into a larger thread of a sufficiently small diameter to permit insertion between the teeth; said thread impregnated with a polymeric coating containing spray-dried flavor particles consisting essentially of a flavor oil dispersed in a matrix of a water-soluble medium with the water-soluble medium being capable of being dissolved by the saliva in the oral cavity when the article is applied to the teeth thereby releasing the flavor to the teeth and oral cavity wherein the polymeric coating is selected from the group consisting of a. alkyl monoesters of poly(methyl vinyl ether/maleic acid) of the formula:

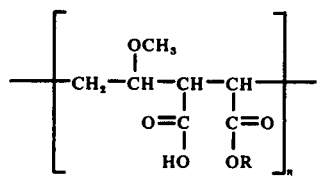

wherein R is an alkyl group containing from 1 to 4 carbon atoms or hydrogen and wherein $n$ is from about 3000 to 3400;

b. polyvinyl pyrrolidones of the formula:

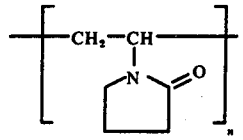

wherein $n$ is from about 100 to 360;

c. acrylamide/acrylate/butylaminoethyl methacrylate polymers;
d. vinyl acetate/crotonic acid/vinyl neodecanoate terpolymers;
e. vinyl acetate/crotonic acid copolymers; and
f. terpolyamides comprised of the copolymerization products of dicarboxylic acid-diamine reaction product, a second but dissimilar dicarboxylic acid-diamine reaction product and a lactam wherein said terpolyamides have a molecular weight of from about 12000 to about 24000.

* * * * *